United States Patent
Belsinger, Jr. et al.

(10) Patent No.: US 9,629,759 B2
(45) Date of Patent: *Apr. 25, 2017

(54) INFANT PATIENT TRANSFER DEVICE WITH VAPOR BARRIER

(71) Applicant: General Electric Company, Schenectady, NY (US)

(72) Inventors: Harry Edward Belsinger, Jr., Forest Hill, MD (US); Steven Mitchell Falk, Baltimore, MD (US); Karen P. Starr, Monkton, MD (US)

(73) Assignee: General Electric Company, Schenectady, NY (US)

( * ) Notice: Subject to any disclaimer, the term of this patent is extended or adjusted under 35 U.S.C. 154(b) by 225 days.

This patent is subject to a terminal disclaimer.

(21) Appl. No.: 14/490,135

(22) Filed: Sep. 18, 2014

(65) Prior Publication Data

US 2016/0081863 A1     Mar. 24, 2016

(51) Int. Cl.
*A47G 9/04* (2006.01)
*A61G 1/003* (2006.01)
(Continued)

(52) U.S. Cl.
CPC ............ *A61G 1/003* (2013.01); *A47D 13/02* (2013.01); *A47D 15/008* (2013.01);
(Continued)

(58) Field of Classification Search
CPC ........ A47G 9/04; A47G 9/0207; A41B 13/06; A47D 15/02; A47D 15/008; A47D 13/08; A47D 5/006; A47D 13/083; A47D 15/003; A47D 13/02; A47D 13/025; A61G 1/01; A61G 1/003; A61G 1/042; A61G 1/013;
(Continued)

(56) References Cited

U.S. PATENT DOCUMENTS

2012/0145754 A1 * 6/2012 Green .................... A62B 5/00
224/158
2013/0340770 A1   12/2013 Starr et al.

FOREIGN PATENT DOCUMENTS

DE       202005009610 U1 *  8/2005
DE       202005009610 U1    8/2005
FR              487858 A     8/1918

OTHER PUBLICATIONS

International Search Report and Written Opinion for PCT/US2015/050155, mail date Dec. 7, 2015, 14 pages.

* cited by examiner

*Primary Examiner* — Ophelia A Hawthorne
(74) *Attorney, Agent, or Firm* — Andrus Intellectual Property Law, LLP

(57) ABSTRACT

A patient transfer device is utilized to transport infant patients between locations within a hospital environment. The patient transfer device includes a center support section and a pair of side sections that can be moved into contact with each other to surround the infant patient. The first and second side sections each include a handle that can be brought into close proximity to each other and can be grasped by a single hand of a clinician. The patient transfer device includes an integrated vapor barrier that can be positioned to at least partially surround the infant when the infant is received on the patient transfer device to reduce evaporative cooling of the infant. The vapor barrier includes a support structure to create a canopy that holds the vapor barrier out of contact with the infant.

17 Claims, 6 Drawing Sheets

(51) Int. Cl.
    *A61G 1/01*          (2006.01)
    *A61G 1/048*        (2006.01)
    *A61G 1/013*        (2006.01)
    *A47D 13/02*        (2006.01)
    *A47D 15/00*        (2006.01)
    *A61G 7/10*         (2006.01)
    *A61F 5/37*         (2006.01)
    *A61G 1/04*         (2006.01)

(52) U.S. Cl.
    CPC .......... *A61F 5/3761* (2013.01); *A61F 5/3776* (2013.01); *A61G 1/01* (2013.01); *A61G 1/013* (2013.01); *A61G 1/042* (2016.11); *A61G 1/048* (2013.01); *A61G 7/1023* (2013.01); *A61G 2200/14* (2013.01); *A61G 2200/32* (2013.01)

(58) Field of Classification Search
    CPC .. A61G 1/048; A61G 7/1023; A61G 2200/14; A61G 2200/32; A61B 19/08; A45F 3/02; A61F 5/3761; A61F 5/3776
    See application file for complete search history.

INFANT PATIENT TRANSFER DEVICE WITH VAPOR BARRIER

BACKGROUND

The present disclosure generally relates to a device for moving an infant patient. More specifically, the present disclosure relates to an infant patient transfer device (sling) that can be used to support an infant patient during movement while including an integrated vapor barrier that can form a canopy around the infant to reduce evaporative cooling of the infant.

Presently, the standard practice used to transfer an infant patient out of an incubator or bed is for a nurse or other care physician to carefully slide a hand (or two) under the infant patient and manually lift the patient. When the nurse physically contacts the infant patient, the patient is often stimulated which, in high risk patients, can introduce unwanted stress to the infant patient. In addition, when a nurse lifts the infant patient, there is an increased risk of the nurse snagging one or more of the multiple lines connected to the patient (IV, EKG leads, ET tube, etc.). The possibility of snagging or disconnecting tubes connected to the infant patient can increase the risk to the infant patient during the lifting procedure.

In order to address these problems, a patient transfer device, such as shown in U.S. Patent Publication No. 2013/0340770 was developed. When a patient is received within the infant patient transfer device, the patient is securely held in place for transport. Currently, there is a trend to delay clamping of the umbilical cord after the baby has been born. In such situations, the infant may be held within the patient transfer device for between one and ten minutes. While the infant is within the patient transfer device, there is no monitoring of the patient vital signs. Once the infant is transported to an infant warmer, patient bed or incubator, sensors are applied to the patient to begin monitoring vital signs.

When an infant is initially born, it has become common practice to place a plastic sheet or blanket around the infant to help the infant retain moisture and prevent evaporative cooling. Since the newborn has just left a fluid environment, the newborn's skin is saturated with fluid. Immediately after birth, the fluid within the newborn's skin begins to evaporate, which causes cooling of the infant. To prevent such cooling, the infant is often wrapped in a fluid impermeable plastic sheet. The plastic sheet typically contacts the skin of the infant, which can cause damage to the skin when the plastic sheet is removed.

SUMMARY

The present disclosure relates to a patient transfer device for moving an infant patient. The patient transfer device securely holds the patient and includes an integrated vapor barrier that can be placed around the infant to prevent evaporative cooling of the infant when the infant is in the patient transfer device.

The patient transfer device includes a center support section that is positioned beneath the patient. First and second side sections are each connected to the center support section. The first side section includes a first handle while the second side section includes a second handle. When an infant patient is supported on the center support section, the first and second side sections can be moved upward and toward each other such that the first and second handles are positioned in close proximity to each other. When the first and second handles are positioned in close proximity to each other, the clinician can grasp both of the first and second handles with a single hand to move the patient while the patient is supported by the patient transfer device.

The patient transfer device further includes a stiffening device that can be positioned within the center support section to provide rigid support for the infant patient during movement. In one embodiment of the disclosure, the stiffening device is a backboard that is received within a pocket formed in the center support section. The backboard can be selectively removed and inserted onto the center section as needed and desired. The backboard preferably extends along a longitudinal axis, wherein the backboard is flexible along the longitudinal axis and rigid in a direction transverse to the longitudinal axis. The rigid nature of the backboard supports the patient's spine during movement while allowing the first and second side sections to move toward each other to securely envelope the patient during transport.

The patient transfer device may further include a hold down device positioned on one of the first and second side sections. The hold down device receives and retains the wires and tubes connected to the patient such that the wires and tubes are securely retained during transport of the patient. Various types of hold down devices are contemplated as being within the scope of the present disclosure. One embodiment includes a section of material that can be connected to the second side section to hold the tubes and wires in place.

The patient transfer device may further include a vapor barrier that can be used to form a canopy over the infant patient when the infant is positioned on the center section of the patient transfer device. The canopy created by the vapor barrier reduces the amount of evaporative cooling of the infant.

In one embodiment, the vapor barrier includes a plastic sheet that can be folded and unfolded between a storage condition and a usage condition. When the plastic sheet is in the folded condition, the vapor barrier can be stored in a pocket formed in the center section. When needed, the vapor barrier is pulled from the pocket and unfolded.

The vapor barrier further includes an integrated support structure that can be manipulated to create a canopy over the infant with the plastic sheet. The support structure includes flexible support members that can be bent into a desired shape to support the plastic sheet.

The vapor barrier can further include a pair of spaced attachment strips located near the side edges of the plastic sheet. The attachments strips hold the plastic sheet in contact with the center section. The vapor barrier can further include a fabric collar to attach the plastic sheet just below the chin of the infant.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE INVENTION

Figure 1:
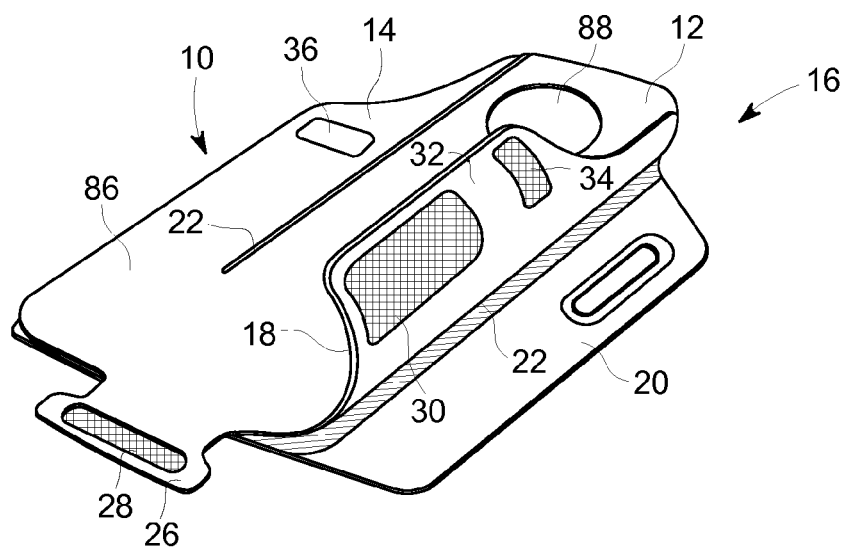
FIG. 1 is a front perspective view of a first embodiment of a patient transfer device of the present disclosure.

FIG. 1 illustrates a patient transfer device 10 of the present disclosure. The patient transfer device 10 can be used to transfer an infant patient from one location to another while minimizing the physical contact between the clinician and the patient while providing secure support for the patient during movement.

Figure 2:
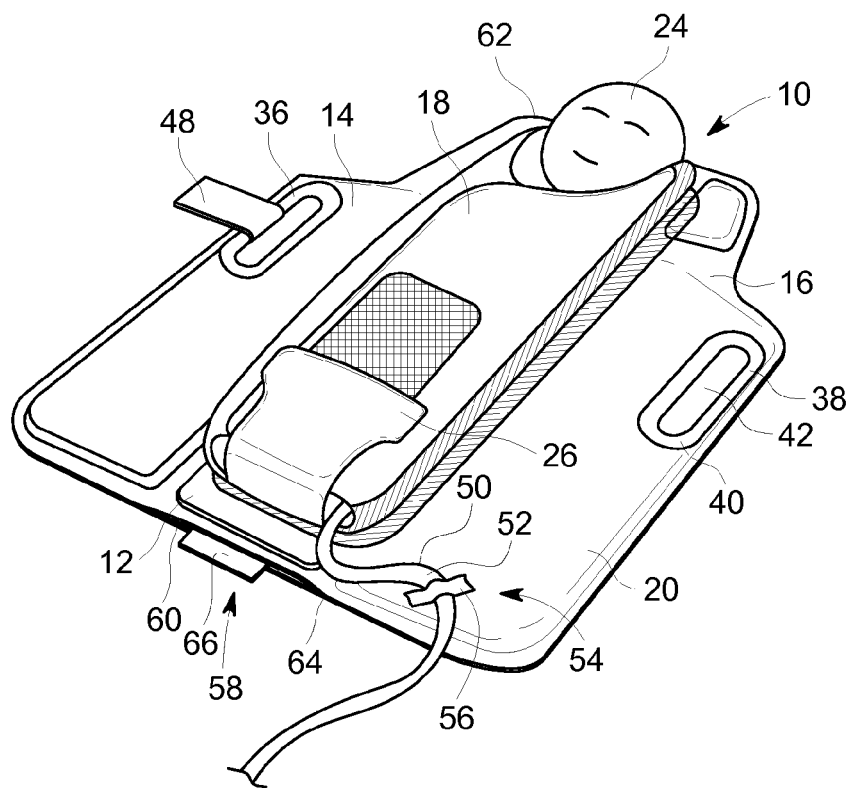
FIG. 2 is a front perspective view of the first embodiment of the patient transfer device with an infant supported on the device.

As illustrated in FIG. 1, the patient transfer device 10 includes a center section 12, a first side section 14 and a second side section 16. In the embodiment illustrated in FIG. 1, the patient transfer device includes an inner liner 18 and an outer liner 20 that each form portions of the center and side sections. Although an inner liner 18 and an outer liner 20 are shown as separate components in FIG. 1, it should be understood that the inner and outer liners 18, 20 could be combined as a single layer that forms the center section 12 and the first and second side sections 14, 16. In the embodiment shown in FIG. 1, the inner liner 18 is formed from a soft, foam material and is joined to the outer liner 20 along a pair of spaced attachment lines 22. The outer liner 20 can be formed from a slightly more rigid and durable material as compared to the inner liner 18. As illustrated in FIG. 2, an infant patient 24 can be placed on the inner liner 18 and the opposite sides of the inner liner 18 that forms a portion of the side sections folded over the patient 24 to surround the patient as illustrated.

In the embodiment shown in FIG. 1, the inner liner 18 includes an extended end portion 26 that includes an end fastener 28. When the patient is supported on the inner liner as shown in FIG. 2, the end fastener 28 formed as part of the end portion 26 is received along a second fastener 30. In the embodiment shown in FIGS. 1 and 2, the fasteners 28, 30 are opposite portions of a hook and loop fastener, such as Velcro®. The physical engagement between the fasteners 28, 30 allows the end portion 26 to fold the inner liner 18 in the condition shown in FIG. 2. Although a hook and loop fastener are shown in the embodiment of FIGS. 1 and 2, it should be understood that different types of fasteners could be utilized while operating within the scope of the present disclosure. Alternatively, the end portion 26 could be eliminated while also operating within the scope of the present disclosure.

Referring back to FIG. 1, the fastener 30 is secured to an inner surface 32 of the inner liner 18 and is exposed only after the second side section of the inner liner is wrapped around the infant patient. In addition to the fastener 30, an upper fastener portion 34 is also positioned along the inner surface 32. The upper fastener portion 34 is engaged by a mating fastener 35 formed along the first side section 14 of the inner liner 18. The fasteners 34, 35 can also be mating, portions of a hook and loop fastener, such as Velcro®. The fasteners 34, 35 aid in holding the first and second side sections of the inner liner 18 in the condition shown in FIG. 2. Although hook and loop fasteners are shown in the embodiment of FIGS. 1 and 2, it should be understood that other types of fasteners could be utilized while operating within the scope of the present disclosure.

As illustrated in FIG. 2, the portion of the outer liner 20 that forms a portion of the first side section 14 includes a first handle 36 while the portion of the outer liner 20 that forms a portion of the second side section 16 includes a second handle 38. In the embodiment shown in FIG. 2, the first and second handles 36, 38 are formed only in the outer liner 20 and are defined by a plastic outer housing 40 that forms an open interior 42.

Figure 3:
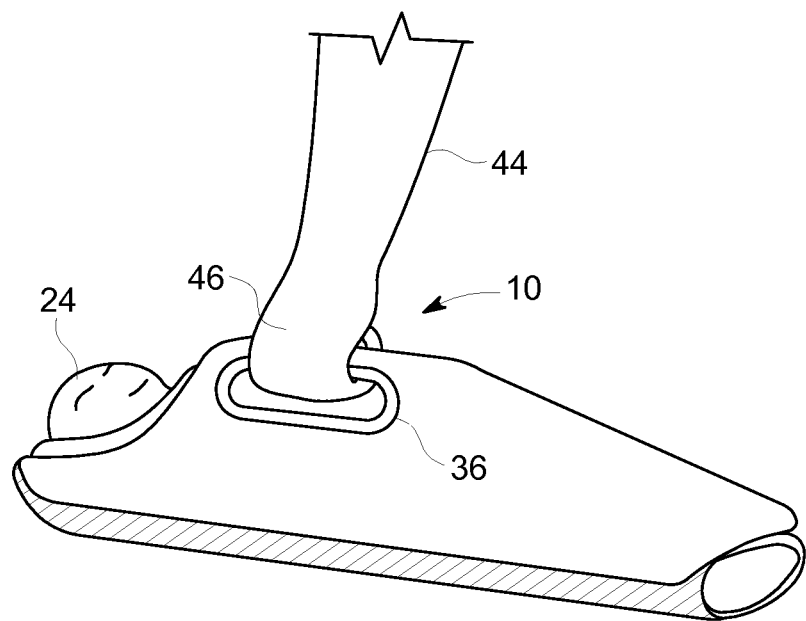
FIG. 3 is a view illustrating the use of the transfer device to move an infant patient.

As can be seen in FIG. 3, when the infant patient 24 is supported along the transfer device 10, a clinician 44 can grasp the pair of handles 36, 38 with a single hand 46 and lift the infant patient for transport and movement. As can be understood in FIGS. 2 and 3, the first and second side sections 14, 16 are sized such that the first and second handles 36, 38 are located close enough to each other to facilitate grasping of the entire patient transfer device 10 by the single hand 46.

Referring back to FIG. 2, in the embodiment illustrated, a strap 48 can be attached to one of the first and second handles 36, 38 and used to secure the handles together during transport of the patient 24. Although a flexible strap 48 is shown in FIG. 2, various other types of straps could be utilized while operating within the scope of the present disclosure. Alternatively, the strap 48 could be eliminated.

As illustrated in FIG. 2, a series of tubes 50 and wires 52 are often attached to the patient 24 that needs to be transported. Since the wires and tubes 50, 52 are often inserted into the patient or connected at specific locations on the patient, it is desirable not to disrupt the tubes and wires during movement. Thus, a need exists for some type of hold down device to prevent the tubes and wires from being disconnected from the patient 24 during transport. In the embodiment shown in FIG. 2, a hold down device 54 is formed on one of the first and second side sections 14, 16 of the transport device. In the embodiment of FIG. 2, a section of adhesive tape 56 is attached to the inner surface of the outer liner 20 in the second side section 16. Although adhesive tape 56 is shown in FIG. 2, other types of hold down devices 54 are contemplated as being within the scope of the disclosure. For example, the hold down device 54 could be a section of a hook and loop fastener, a strap with a button on snap, a section of flexible material or any other type of device that could be utilized to hold the tubes and wires 50, 52 in a secure position as illustrated.

In the embodiment shown in FIG. 2, a stiffening device 58 is shown inserted into a pocket 60 formed in the center section 12 of the patient transfer device 10. The stiffening device 58 typically extends the entire length of the center section 12 from the first end 62 near the patient's head to a second end 64 near the feet of the patient. The stiffening device 58 provides the required stiffness for the patient transfer device 10 such that when the patient transfer device 10 is used to support the patient, the stiffening device 58 prevents the first and second side sections 14, 16 from collapsing onto the patient 24. Additionally, the stiffening device 58 provides the required stiffness for the transfer device 10 such that the transfer device and the patient do not collapse in the longitudinal direction between the first end 62 and the second end 64.

In the embodiment shown in FIGS. 1 and 2, the stiffening device 58 is a backboard that is received within the pocket 60 and extends the entire length of the patient transfer device 10 from the first end 62 to the second end 64. The backboard 66 is preferably formed from a plastic material that has the required stiffness, durability and size to provide the required support for the infant patient 24. Although plastic is described as being the most preferred material for the backboard 66, it is contemplated that other materials could be utilized while operating within the scope of the present disclosure.

Alternatively, the removable stiffening device 58 and sewn-in pocket 60 could be replaced with other types of stiffening devices. As an example, a series of inflatable tubes could be formed within the center section 12 and selectively inflated/deflated depending upon whether the patient 24 is on the transfer device 10 and needs to be moved. Various other types of stiffening devices are also contemplated as being within the scope of the present disclosure. The use of the stiffening device 58 is contemplated as being valuable to provide secure and stable support for the infant patient 24 during movement.

Figure 4:
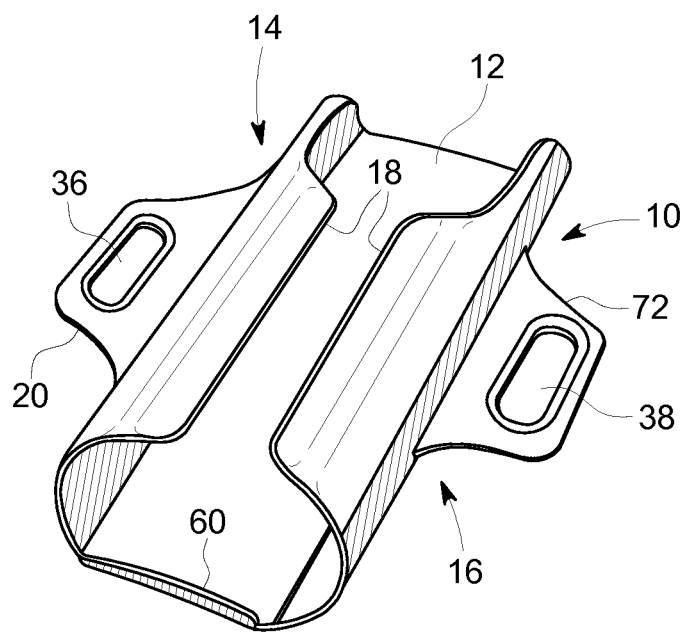
FIG. 4 is a front perspective view of a second, alternate embodiment of the patient transfer device.
Figure 5:
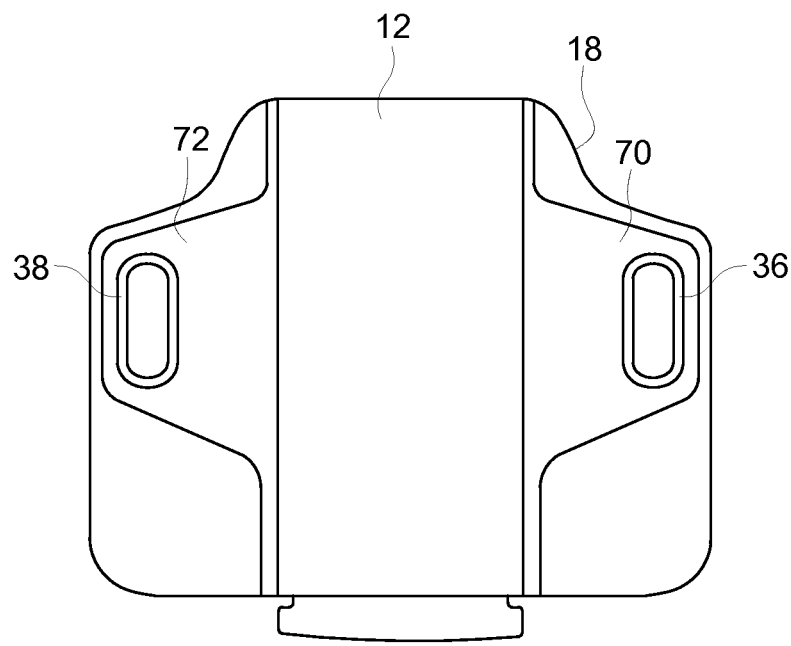
FIG. 5 is a back view of the patient transfer device shown in FIG. 4.

FIGS. 4 and 5 illustrate a second embodiment of the patient transfer device 10 of the present disclosure. In the second embodiment shown in FIG. 4, the center section 12 also includes the pocket 60. In the embodiment shown in FIGS. 4 and 5, the first side section 14 includes the inner liner 18 and a smaller, outer liner 70, Likewise, the second side section 16 includes the inner liner 18 and smaller, outer liner 72. The outer liners 70, 72 include the first and second handles 36, 38 as in the first embodiment shown in FIGS. 1-2.

Figure 6:
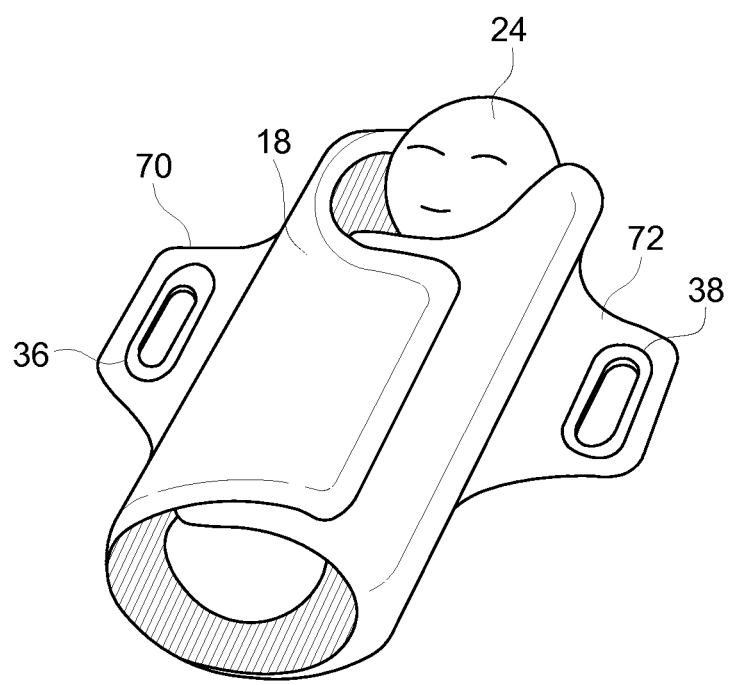
FIG. 6 is a view of the alternate embodiment of the patient transfer device used to support an infant.
Figure 7:
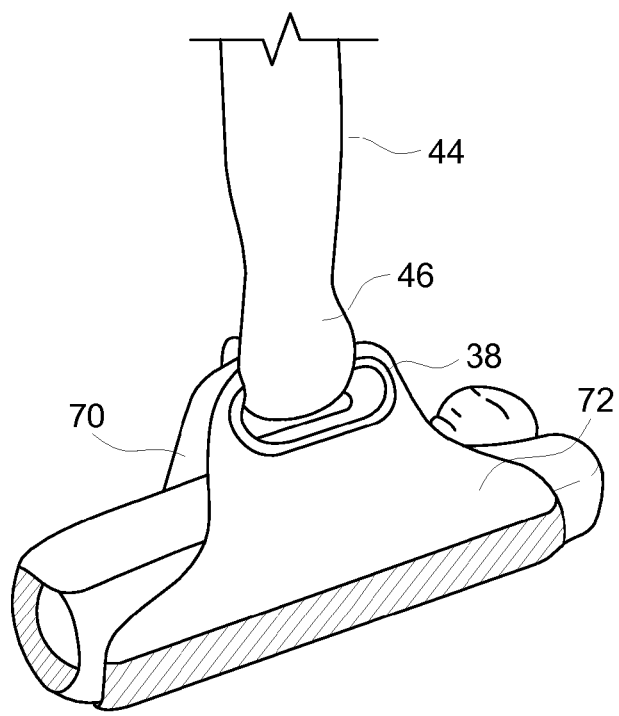
FIG. 7 is a view showing the transport of an infant patient using the transfer device using of the present disclosure.

As illustrated in the back view of FIG. 5, the outer liner sections 70, 72 are joined to the center section 12. As in the first embodiment, the inner liner 18 is formed from a soft, foam material that provides a comfortable support surface for an infant patient when the infant patient is supported on the inner liner 18. As illustrated in FIG. 6, the patient 24 is supported along the center section and the inner liner of both the first and second side sections are wrapped around the patient 24. Although not illustrated, it is contemplated that various types of fastening devices and materials could be utilized to hold the opposite sides of the inner liner 18 in place as shown. When the patient 24 is wrapped within the inner liner 18 as illustrated in FIG. 7, the outer liner sections 70, 72 of the first and second side sections can be brought together such that a single hand 46 of the clinician 44 can be used to grasp both handles.

Figure 8:
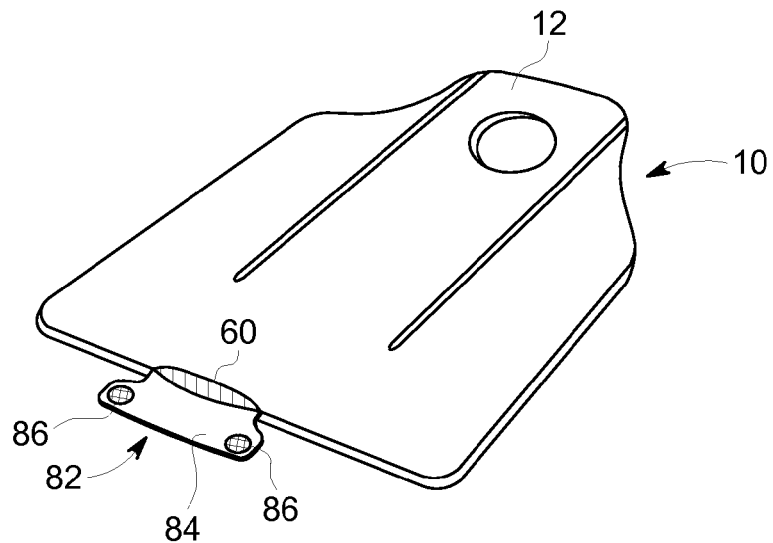
FIG. 8 is a front perspective view of the patient transfer device showing the initial removal of the vapor barrier.

FIG. 8 illustrates an embodiment of the patient transfer device 10 that includes an integrated vapor barrier 82 that can be used to wrap the infant, patient to limit and reduce evaporation from the skin of the infant following birth. In the embodiment shown in FIG. 8, the vapor barrier 82 is shown being pulled from within the internal pocket 60 formed in the center section 12. The vapor barrier 82 includes a collar portion 84 that is shown in FIG. 8 as being pulled from within the pocket 60. The collar portion 84 is formed from a fabric material and includes a pair of releasable fasteners 86 formed on each end of the collar 84. In the embodiment illustrated, each of the releasable fasteners 86 can be One half of a hook and loop fastener, such as Velcro.

Figure 9:
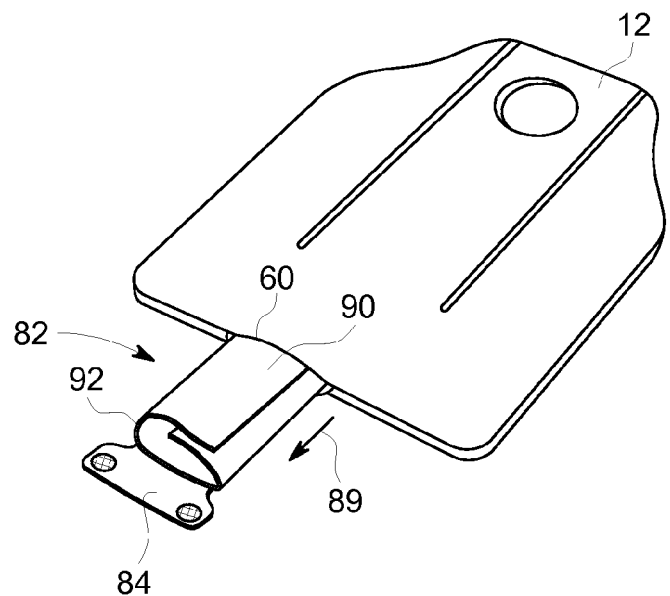
FIG. 9 is a front view showing the further removal of the vapor barrier.

As illustrated in FIG. 9, the vapor harrier 82 can be pulled further from within the center section 12 in the direction shown by arrow 89. The vapor barrier 82 shown in FIG. 9 includes a plastic sheet 90 that is folded upon itself and which has the collar portion 84 securely attached to its outer end 92. The vapor barrier 82 can be folded in any manner and is stored within the open pocket 60 formed in the center section 12.

Figure 10:
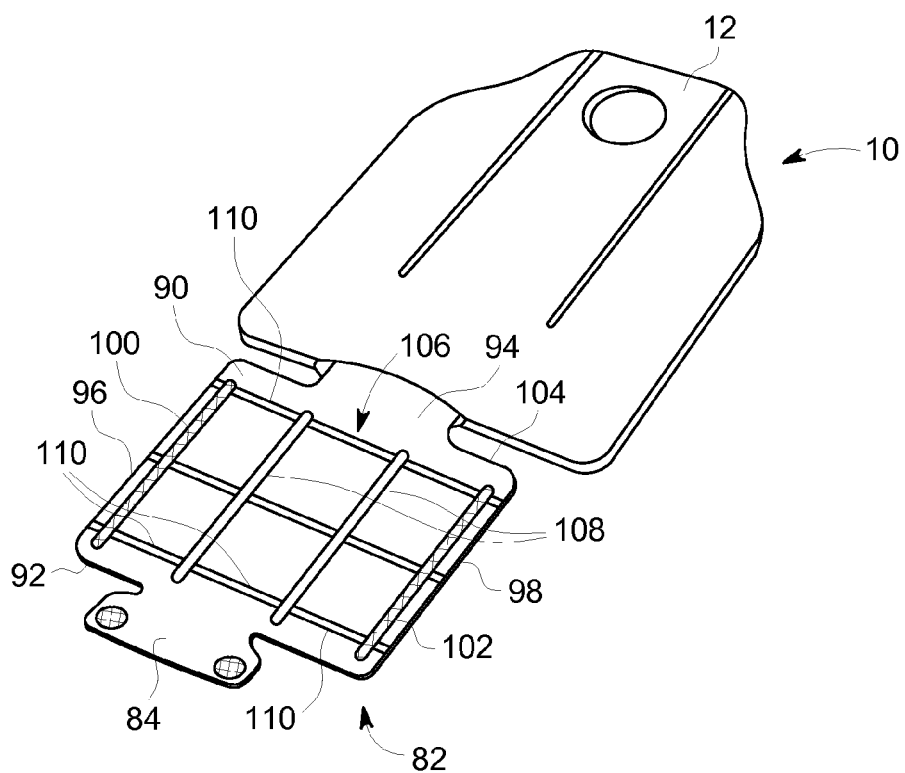
FIG. 10 illustrates the vapor barrier in its unfolded condition.

FIG. 10 illustrates the vapor barrier 82 in its full unfolded condition. In this unfolded condition, the plastic sheet 90 remains coupled to the center section 12 by an attachment portion 94. The plastic sheet 90 has a width that extends between a first side edge 96 and a second side edge 98. The plastic sheet 90 is connected to the fabric collar portion 84.

The vapor barrier 82 includes a pair of spaced side attachment strips 100, 102. Each of the side attachment strips 100, 102 extends along the length of the plastic sheet from the inner end 104 to the outer end 92. The attachment strips 100, 102 can be formed from a hook and loop fastening material, such as Velcro. Each of the side attachment strips 100, 102 is positioned close to one of the first and second side edges 96, 98.

In the embodiment shown in FIG. 10 the plastic sheet 90 that forms part Of the vapor barrier 82 includes a support structure 106. The support structure 106 in the embodiment shown in FIG. 10 is a grid-like structure that is attached to either the top or bottom surface of the plastic sheet 90. The support structure shown in FIG. 10 includes a pair of longitudinal rods 108 that each extend parallel to one of the side edges 96, 98. In the embodiment shown, each of the rods 108 is formed from a flexible, bendable material that can retain a shape in a desired position dictated by the caregiver.

In addition to the rods 108, the support structure 106 includes a series of individual cross supports 110. The cross supports 110 are also formed from a bendable, semi-rigid material that can be bent into a desired shape and include enough material memory to remain in the selected position. As one illustrative example, the cross supports 110 could be formed from a thin, wire material that can be bent into a desired shape and will retain the desired shape unless further deflected. In the embodiment shown in FIG. 10, the support structure 106 is formed from the pair of rods 108 and a series of nine individual cross supports 110. Although nine cross supports 110 are shown in the embodiment of FIG. 10, it should be understood that fewer or greater number of cross supports 110 could be utilized depending upon the requirements of the patient transfer device.

The support structure 106 could be either heat welded to the plastic material, adhesively attached to the plastic sheet 90 or entrapped between a pair of upper and lower plastic sheets. In each case, the support structure 106 is designed such that the vapor barrier 82 can be folded into a storage condition for receipt in the pocket 60 and unfolded into the usage condition shown in FIG. 10.

Figure 11:
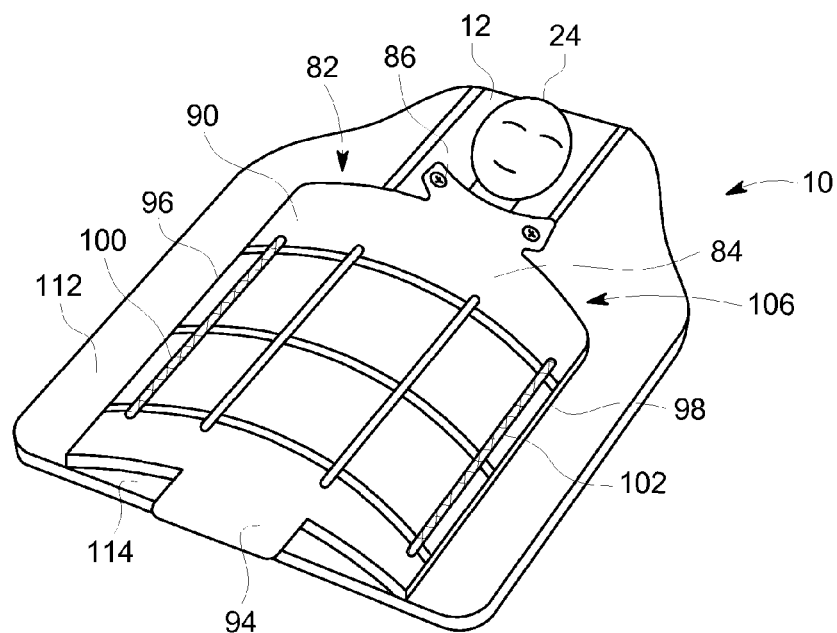
FIG. 11 illustrates the position of the vapor barrier to create a canopy over an infant.

Referring now to FIG. 11, when the infant 24 is positioned on the patient transfer device 10, the vapor barrier 82 can be tented to create a canopy over the infant. In such a usage condition, each of the side attachment strips 100 attaches the side edges 96, 98 of the plastic sheet 90 to an inner surface 112 of the center section 12 (see FIG. 12). Prior to attaching each of the side edges to the inner surface 112, the caregiver bends the support structure 106 in a manner shown in FIG. 11 to create a tented canopy over the infant 24. When the canopy is created, the plastic sheet 90 is spaced slightly above the infant and does not contact the skin of the infant. The support structure 106 has enough strength and structural stability to create an air gap between the plastic sheet 90 and the skin of the infant while creating a harrier to reduce evaporation of moisture.

As illustrated in FIG. 11, when the canopy has been created by the support structure 106 and the plastic sheet 90, the collar portion 84 is brought up near the neck of the infant 24. In this condition, the releasable fasteners 86 also engage the inner surface 112 of the center section 12 to hold the collar portion 84 in position as shown. In the preferred embodiment of the disclosure, the collar portion 84 is formed from a fabric material that creates a soft interface between the vapor barrier 82 and the infant patient 24.

As illustrated in FIG. 11, the support structure 106 creates a canopy over the infant that includes an air gap 114 between the plastic sheet 90 and the infant. This air gap 114 prevents contact between the plastic sheet and the infant to prevent skin irritation while creating a vapor barrier to reduce evaporative cooling from the infant.

Figure 12:
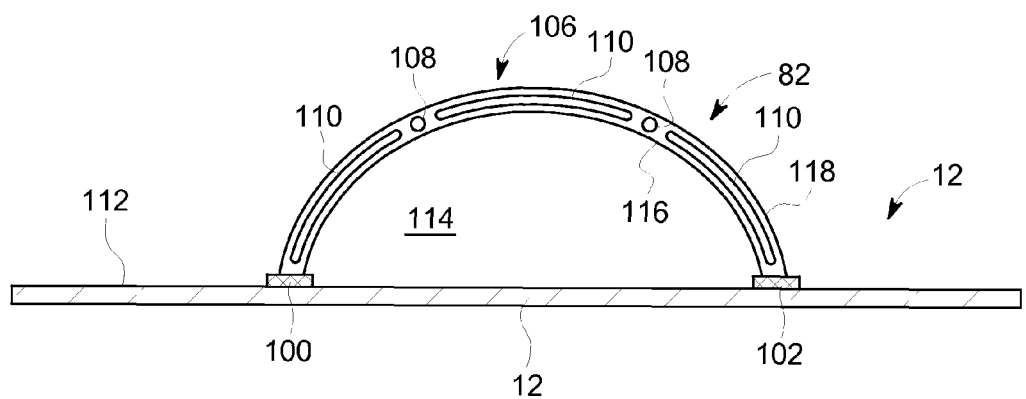
FIG. 12 is a section view showing the position of the canopy created by the vapor barrier.

FIG. 12 is a cross section through the patient transfer device 12 illustrating the open air gap 114 created by the support structure 106, including the pair of spaced rods 108 and cross supports 110. The support structure 106 is shown in FIG. 12 as sandwiched between an inner plastic sheet 115 and an outer plastic sheet 118. Although inner and outer plastic sheets 116, 118 are shown in the drawing figure, it should be understood that only a single plastic sheet could be utilized while operating within the scope of the present disclosure. As illustrated in FIG. 12, the side attachment strips 100, 102 hold the vapor barrier 82 into contact with the inner surface 112 along the center section 12. The size of the air gap 114 between the inner surface 112 and the plastic sheets is dictated by the configuration of the support structure 106.

Although the vapor barrier 82 is shown as being folded arid concealed within the open pocket 60 formed in the center section, it should be understood that the vapor barrier could also be connected to different portions of the patient transfer device. As one example, it is contemplated that the vapor barrier could connect to the handles and extend across the open interior and cover the infant. However, in each embodiment, the vapor barrier is connected to the patient transfer device and can be selectively positioned over the infant as desired. In each case, it is desired that the vapor barrier be spaced from the skin of the infant to prevent irritation to the skin of the infant by the plastic sheet.

Referring back to FIGS. 1 and 2, the method of utilizing the patient transfer device 10 of the present disclosure will now be described. Although the present method is being described as one preferred method of utilizing the patient transfer device 10, it should be understood that the patient transfer device 10 could be utilized in different ways depending upon the clinician requirement and the desired amount of movement necessary for the patient 24.

Initially, the patient transfer device 10 is positioned within an incubator or patient bed before the patient is placed within the incubator or bed. It is contemplated that the patient transfer device 10 could be placed in an incubator in situations in which the patient will be moved frequently by the clinician.

Once the patient transfer device 10 is placed within the incubator, the patient is placed on the outer surface 86 of the inner liner 18 in the center section 12. In the embodiment illustrated, the inner liner 18 includes a headrest 88 that includes additional cushioning for the patient's head. However, the headrest 88 could be eliminated while operating within the scope of the present disclosure.

If it is desired to move the patient 24, the clinician initially installs or activates the stiffening device 58 within the center section 12. In the embodiment shown in FIG. 2, the stiffening device 58 is a backboard 66 which is inserted into the open pocket 60 formed in the center section 12. Although a backboard 66 is shown in the embodiment, other types of stiffening devices could be utilized while operating within the scope of the present disclosure. It is desirable that the stiffening device 58 can be selectively removed to increase the comfort of the patient 24 if simply resting within a bed or incubator.

As described previously, it is desired that the backboard 66 be inflexible in a direction transverse to the lengthwise, longitudinal axis of the backboard 66. The rigid, inflexibility of the backboard 66 in a direction transverse to the longitudinal axis provides additional support for the back and spine of the patient during transport. However, it is also desirable that the backboard 66 be somewhat flexible toward the longitudinal axis so that when the first and second side sections are lifted over the patient, the backboard slightly flexes to increase the comfort for the patient.

If the caregiver determines that it is desirable to reduce evaporative cooling of the patient, the caregiver can utilize the vapor barrier 82 stored within the patient transfer device. As shown in FIG. 8, the caregiver can pull the fabric collar 84 from within the open pocket 60 and unfold the vapor barrier as illustrated in FIG. 10. Once the vapor barrier 82 has been unfolded as shown in FIG. 10, the support structure 106 can be bent to create a canopy that is placed over the infant as shown in FIG. 11. When the canopy created by the vapor barrier 82 is positioned over the infant as shown in FIG. 11, each of the side attachment strips 100, 102 engage the inner surface 112 to hold the canopy created by the vapor barrier in place.

Once the vapor barrier is in place, the fabric collar 84 is attached to the inner surface by the pair of flexible fasteners 86. Once the canopy has been created by the vapor barrier, the side handles can be grasped by the caregiver, as shown in FIG. 7, to carry the infant to the desired location.

Once the infant has been transported to the desired location, the vapor harrier 82 can be removed and restored within the open pocket formed in the center section. As can be understood by the previous description, the canopy created by the support structure formed as part of the vapor barrier prevents contact between the plastic sheet of the vapor barrier and the infant while preventing evaporation and cooling of the infant.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A transfer device for supporting an infant patient during transport of the patient, comprising:
   a center support section positionable beneath the patient during transport of the patient;
   a first side section connected to the center support section and including a first handle; and
   a second side section connected to the center support section and including a second handle, wherein the first and second side sections are movable toward each other to surround the patient; and
   a vapor barrier movable between a storage condition and a use condition, wherein the vapor barrier is configured to form a canopy in the use condition that at least partially surrounds the patient to reduce the effects of evaporative cooling of the patient when the patient is supported on the center support section, wherein the vapor barrier is separate from the first and second side sections.

2. The transfer device of claim 1 wherein the vapor barrier includes support structure to hold the canopy formed by the vapor barrier away from contact with the patient.

3. The transfer device of claim 2 wherein the support structure is securely attached to a plastic sheet.

4. The transfer device of claim 3 wherein the support structure is formed from a plurality of flexible support members.

5. The transfer device of claim 1 wherein the vapor barrier comprises a plastic sheet.

6. The transfer device of claim 5 wherein the plastic sheet includes a pair of spaced side attachment strips.

7. The transfer device of claim 1 wherein the vapor barrier is received within a pocket formed in the center section in the storage condition.

8. The transfer device of claim 1 wherein the vapor barrier includes a collar portion positionable in contact with the patient and removably connected to the center section.

9. A transfer device for supporting an infant patient during transport of the patient, comprising:
 a center support section positionable beneath the patient during transport of the patient;
 a first side section connected to the center support section;
 a second side section connected to the center section, wherein the first and second side sections are sized to surround the patient when the first and second side sections are folded toward each other when the patient is on the center section; and
 a vapor barrier movable between a storage condition and a use condition, wherein the vapor barrier includes an integrated support structure, wherein the vapor barrier and support structure form a canopy separately from the first and second side sections that surrounds the patient to reduce the effects of evaporative cooling of the patient when the patient is supported on the center support section.

10. The transfer device of claim 9 wherein the support structure is securely attached to a plastic sheet.

11. The transfer device of claim 10 wherein the support structure is formed from a plurality of flexible support members.

12. The transfer device of claim 9 wherein the vapor barrier is received within a pocket formed in the center section in the storage condition.

13. The transfer device of claim 9 wherein the plastic sheet includes a pair of spaced side attachment strip.

14. A method of transporting an infant patient, comprising the steps of:
 positioning a transfer device beneath the patient, the transfer device including a center support section and first and second side sections joined to the center section, wherein the infant is positioned on the center support section;
 removing a vapor barrier from a storage condition in which the vapor barrier is stored within the center section;
 creating a canopy surrounding the infant with the vapor barrier at least partially attached to the center support section when the infant is positioned on the center support section;
 lifting both the first and second side sections such that the first and second side sections surround the infant patient;
 grasping a first handle formed in the first side section and a second handle formed in the second side section; and
 lifting the transfer device and the infant patient.

15. The method of claim 14 further comprising the step of manipulating a support structure of the vapor barrier to create the canopy such that the vapor barrier is spaced from the infant patient by an air gap.

16. The method of claim 15 wherein the support structure includes a plurality of flexible cross supports.

17. The method of claim 15 wherein the support structure is attached to a plastic sheet such that the combination of the support structure and the plastic sheet for the canopy.

* * * * *